United States Patent [19]

Vofsi et al.

[11] 4,206,235
[45] Jun. 3, 1980

[54] NOVEL 2,5-DIHALOPHENYL-β-SUBSTITUTED SULFONE FUNGICIDES

[75] Inventors: David Vofsi; Yael Allingham, both of Rehovot, Israel

[73] Assignee: Yeda Research & Development Co., Ltd., Rehovot, Israel

[21] Appl. No.: 824,394

[22] Filed: Aug. 15, 1977

[30] Foreign Application Priority Data

Aug. 17, 1976 [IL] Israel .........................................50282
Aug. 17, 1976 [IL] Israel ......................................... 50283

[51] Int. Cl.² ................... A61L 13/00; C07C 147/06; C07C 147/115; C08F 114/06
[52] U.S. Cl. ...................................... 424/337; 424/78; 424/308; 560/11; 568/35; 568/34; 525/3; 525/5
[58] Field of Search .................... 260/607 AR, 607 A; 424/337, 308, 78; 560/11; 526/3, 5

[56] References Cited

U.S. PATENT DOCUMENTS

| | | | |
|---|---|---|---|
| 2,793,234 | 5/1957 | Metivier | 260/607 AR |
| 3,144,383 | 8/1964 | Aichenegg et al. | 424/337 |
| 3,242,041 | 3/1966 | Aichenegg et al. | 424/337 |
| 3,418,101 | 12/1968 | Buchholz et al. | 260/607 AR |
| 3,441,614 | 4/1969 | Asscher et al. | 260/607 AR |
| 4,059,635 | 11/1977 | Sugiyama et al. | 260/607 AR |
| 4,089,964 | 5/1978 | Sugiyama et al. | 424/337 |

FOREIGN PATENT DOCUMENTS

| | | | |
|---|---|---|---|
| 2051117 | 4/1972 | Fed. Rep. of Germany | 424/337 |
| 2203791 | 8/1972 | Fed. Rep. of Germany | 260/607 AR |
| 40-827365 | 4/1965 | Japan . | |
| 40-1059865 | 5/1965 | Japan . | |
| 40-1487765 | 7/1965 | Japan . | |

OTHER PUBLICATIONS

Chemical Abstracts 59:7411h; Nambara et al.
Chemical Abstracts 69:35620d; Tanimoto et al.
Chemical Abstracts 78:136288t; Schroth et al.
Chemical Abstracts 75:109984; J. Org. Chem. (1971), 36(17) 2536-2538; Truce et al.

Primary Examiner—Alton D. Rollins
Assistant Examiner—M. C. Eakin
Attorney, Agent, or Firm—Hubbell, Cohen, Stiefel & Gross

[57] ABSTRACT

The present invention relates to novel 2,5-dihalophenyl-β-substituted sulfone compounds of the formula

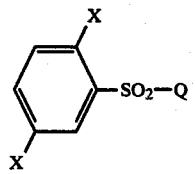

wherein Q is selected from

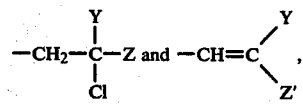

and wherein:
X designates chlorine or bromine,
Y designates hydrogen, chlorine, or bromine,
Z designates chlorine, bromine, phenyl, halophenyl or —COOR wherein
  R is a lower alkyl group of up to and including 4 carbon atoms,
Z' designates chlorine, bromine or —COOR, wherein
  R is a lower alkyl of up to and including 4 carbon atoms, provided that when
  Y is hydrogen, Z' designates —COOR, as herein defined, and to pesticides and especially fungicides containing a compound as defined above as active ingredient. The above compounds are also effective antifungal agents when incorporated in polymeric compositions.

16 Claims, No Drawings

NOVEL 2,5-DIHALOPHENYL-β-SUBSTITUTED SULFONE FUNGICIDES

FIELD OF THE INVENTION

The present invention relates to novel 2,5-dihalophenyl β-substituted haloethyl sulfones and 2,5-dihalophenyl β-substituted vinyl sulfones, to the production of these, to pesticides and especially fungicides containing same as active ingredients and to the use of certain of the novel compounds as antifungal additives to certain polymeric materials (plastics) and paints and as antifungal agents for use in the protection of materials such as cloth and leather. The above defined haloethyl sulfones can be used as starting materials for the production of the halovinyl sulfones of the present invention.

STATE OF THE PRIOR ART

Halogenated alkyl sulfones are known to possess pesticidal properties. Thus German Patent No. 952,479 (C.A., 53:3588d), discloses 2-chloroethyl polyphenyl sulfones for combatting fungi, German Patent No. 2,051,117 also discloses certain, α,β-trichloroethyl halophenyl sulfone fungicides. U.S. Pat. No. 3,437,685 discloses certain dihaloalkyl sulfones as useful for the control of insects, mites, fish, bacteria, fungi, gastropods and plants. Japanese Patent No. 16678/65 discloses specific 2,4-disubstituted phenyl haloethyl sulfones as soil and seed disinfectants and fungicides. French Patent No. 1,584,546 discloses haloalkyl benzyl sulfones having a variety of biocidal activities.

Haloalkylsulfones have also been known to be intermediates for the preparation of vinyl sulfones, which also have utility as pesticides. Thus, for example, U.S. Pat. No. 3,242,041 describes the preparation of 3,4-dichlorophenyl vinyl sulfones from 3,4-dichlorophenyl-2-chloroethyl sulfone by means of dehydrochlorination. Tanimoto, Shigeo, et al. (C.A. 69:35620d), reports the synthesis of β-chlorovinyl sulfones from β,β-dichloroethyl sulfones without suggesting any utility for his compounds.

Israel Pat. No. 20106, U.S. Pat. No. 3,441,614, U.K. Pat. No. 1,087,879, French Pat. No. 1,425,317, German Pat. Appln. No. 5,182,384 discloses a general process for preparing phenyl-β-chloroethyl sulfones and reports the preparation of p-chloro-phenyl-β-chloroethyl sulfones.

Phenylvinyl sulfones have been known for some time to possess pesticidal properties, particularly against fungi and nematodes. Thus, for example, U.S. Pat. Nos. 3,144,383 and 3,242,041 disclose a number of phenylvinyl sulfone compounds for use against nematodes and fungi, respectively. Also U.S. Pat. No. 2,793,234 discloses arylvinyl sulfone fungicides having α,β-dichlorosubstituents on the vinyl group, and U.S. Pat. No. 3,418,101 claims certain phenyl α,β-dihalovinyl sulfones as plant dessicants. Japanese patents publications Nos. 8273/65, 10,598/65, 14,877/65, all in the name of Nippon Soda Co. Ltd., describe certain phenyl chlorovinyl sulfones having germicidal, fungicidal, bactericidal and insecticidal properties.

Phenyl chlorovinyl sulfones have also been disclosed as useful chemicals and intermediates, as for example, in East German Pat. No. 93,559 (Chem. Abst. vol. 78-136288t) and Israel Patents Nos. 20106 and 36120.

SUMMARY OF THE INVENTION

The present invention relates to novel 2,5-dihalophenyl β-substituted haloethyl sulfones and 2,5-dihalophenyl β-halovinyl sulfones, to the production of these, to pesticides containing these as active ingredients, and especially to the use of the novel compounds as fungicides or fungistats.

The novel compounds are of the general formula

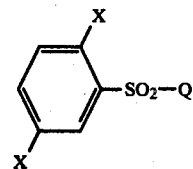

wherein Q is selected from

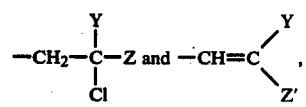

and wherein:
  X designates chlorine or bromine,
  Y designates hydrogen, chlorine or bromine,
  Z designates chlorine, bromine, phenyl, halophenyl or —COOR wherein
  R is a lower alkyl group of up to and including 4 C-atoms,
  Z' designates chlorine, bromine or —COOR, wherein
    R is a lower alkyl of up to and including 4 carbon atoms,
provided that when Y=H, Z designates —COOR as defined above.

The term halophenyl designates as preferred meaning chlorophenyl and bromophenyl, the term lower alkyl includes methyl, ethyl, propyl, isopropyl, butyl, isobutyl. Preferred compounds are the 2,5-dihalophenyl β-substituted haloethyl sulfones of the formula

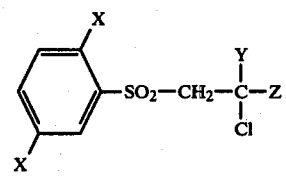

wherein X, Y and Z are as defined above.

Preferred compounds are 2,5-dihalophenyl β,β', β'''-trihaloethyl sulfones, and especially those wherein "halo" designates chlorine; the 2,5-dihalophenyl-β-carboxyalkyl-β'-haloethyl sulfones and particularly 2,5-dichlorophenyl-β-carboxymethyl-β-chloroethyl sulfone, 2,5-dichlorophenyl-β,β'-dichlorovinyl sulfone and 2,5-dihalophenyl-β-carboxymethyl vinyl sulfones, wherein "halo" designates chlorine or bromine.

The 2,5-dihalophenyl-β-substituted haloethyl sulfones can easily be prepared by the redox-transfer reaction of the 2,5-dihalobenzene sulfonyl chloride with the proper olefin in the presence of a catalyst, such as cupric chloride and chloride ions with or without copper bronze. Purer compounds and better yields are obtained with copper bronze as an addition to the catalyst.

The 2,5-dihalophenyl-β-halovinyl sulfones can be readily prepared by the dehydrohalogenation of the appropriately corresponding haloethyl sulfone or by any of the methods described in the above mentioned publications.

The novel 2,5-dihalophenyl-β-substituted haloalkyl sulfones of this invention show remarkable effectiveness as fungicides.

Their fungicidal activity is far superior to that exhibited by the known mono-chlorophenyl and other substituted phenyl-β-chloroethyl sulfones.

According to the invention there are provided novel compositions containing the novel 2,5-dihalophenyl-β-substituted-haloalkyl sulfones as active ingredients.

Compositions containing the above compounds have shown effectiveness against fungi which cause substantial losses to agricultural crops. Amongst these may be mentioned *Rhizoctonia solani, Rhizopus stolonifer, Puccinia coronata, Fusarium oxysporum, Botrytis cinerae, Plasmopara viticola, Piricularia oryzae, Pythium sp., Venturia inaequalis.*

Compounds of this invention may also be used as fungicides in paints and in plastic compositions, as for example, PVC compositions, which are susceptible to attack by micro-organisms, such as the common moulds, *Pencillium funiculosum, Trichoderma viride, Aspergillus niger, A. flavus, Alternaria tenuis, Cladosporium cladosporoides.*

The novel 2,5-dihalophenyl-β-substituted vinyl sulfones according to the present invention are effective pesticides, and they have a pronounced fungicidal and acaricidal activity.

Compositions containing the above 2,5-dihalophenyl-β-substituted vinyl sulfones have shown effectiveness against fungi which cause substantial losses to agricultural crops. Amongst these may be mentioned *Rhizoctonia solani, Rhizopus stolonifer,* and particularly, *Fusarium oxysporum f. lycopersici,* and *Pythium sp.*

2,5-dichlorophenyl-β, β'-dichlorovinyl sulfone, in particular, has shown a strong activity against the two-spotted mite.

DESCRIPTION OF THE PREFERRED EMBODIMENTS

The invention is illustrated with reference to the following illustrative Examples, which are to be construed in a non-limitative manner.

EXAMPLE 1

2,5-dichlorophenyl-β,β'-dichloroethyl sulfone

A solution of 50 g of 2,5-dichlorobenzene sulfonyl chloride in 50 ml methylene chloride and a solution of 0.4 cupric chloride and 0.6 g triethyl ammonium chloride were introduced into a glass lined autoclave. To this was added a solution of 50 g vinyl chloride at about −50° C. After removal of air the autoclave was closed and the temperature was raised to 110° C. The pressure was 350 p.s.i. after keeping at 110° C. for 12 hours, the reaction mixture was cooled and washed with 15% HCl solution followed by water and dried with sodium sulfate. After removal of the solvent the solid was recrystallized from isopropanol. Yield: 50% M.P.: 103° C.

EXAMPLE 2

2,5-dichlorophenyl,β,β',β''-trichloroethyl sulfone

A solution of 25 g 2,5-dichlorobenzene sulfonyl chloride, 40 g vinylidene chloride 0.2 g cupric chloride + 0.2 g copper bronze, 0.3 g triethylammonium chloride and 10 ml acetonitrile were introduced into a glass lined autoclave and heated at 120° C. for 12 hours. After cooling, the reaction mixture was washed with 15% HCl, followed by water. After drying over sodium sulphate the solvent was removed. The product was recrystallized from isopropanol. Yield: 70%, M.P.: 114° C.

EXAMPLE 3

2,5-dichlorophenyl-β-carboxymethyl-β'-chloroethyl sulfone 25 g 2,5-dichlorobenzene sulfonyl chloride, 28 g methyl acrylate, 0.2 g cupric chloride + 0.2 copper bronze, 0.6 g triethyl ammonium chloride and 10 ml acetonitrile refluxed for 8 hours. After cooling, the product was recrystallized from isopropanol. Yield: 75%, M.P.: 69° C.

EXAMPLE 4

2,5-dichlorophenyl-β, β-dichlorovinyl sulfone

To a solution of 3 g 2,5-dichlorophenyl-β,β,β,-trichloroethyl (Example 2) sulfone in 50 ml methylene chloride there was added 1 g of triethylamine. After standing at room temperature for 1 hour the solution was washed with water. After drying over sodium sulfate the solvent was removed. The product, 2,5-dichlorophenyl-β,β-dichlorovinyl sulfone, was recovered by recrystallization from isopropanol. Yield: 85%, M.P.: 119° C.

EXAMPLE 5

2,5-dichlorophenyl-β-chloro-β-phenylethyl sulfone 25 g 2,5-dichlorobenzene sulfonyl chloride 0.2 g cupric chloride 0.3 g triethylammonium chloride 10 ml acetonitrile and 10 g styrene were refluxed for 3 hours. On cooling, the contents were recrystallized for ethanol. Yield: 90%, M.P.: 136° C.

EXAMPLE 6

2,5-dichlorophenyl-β-chloro-β-bromoethyl sulfone

A solution of 25 g 2,5-dichlorobenzene sulfonyl chloride in 50 ml methylene chloride and a solution of 0.2 cupric chloride and 0.3 g triethylammonium chloride in 10 ml acetonitrile were sealed in a Carius tube, with 30 g vinyl bromide. The tube was kept at 120° C. for 24 hours. After cooling, the reaction product was washed with 15% HCl solution and then with water. After drying on sodium sulphate, the solvent was removed by distillation. The product was recrystallized from isopropanol and had a M.P. of 112° C. The yield was 37%.

EXAMPLE 7

2,5-dibromophenyl-β,β'-dichloroethyl sulfone

A sulfone of 34 g 2,5-dibromobenzene sulfonyl chloride in 50 ml methylene chloride and a solution of 0.2 g cupric chloride and 0.3 g triethylammonium chloride in 10 ml acetonitrile were cooled and a solution of 16 g vinyl chloride in 50 ml methylene chloride, cooled in dry ice, was added. The mixture was introduced into a glass lined autoclave which was purged with nitrogen. After sealing the autoclave the temperature was raised to 120° C. and kept for 12 hours.

After cooling, the contents of the autoclave were treated as the reaction product in Example 1. Yield: 70%, M.P.: 104° C.–105° C.

EXAMPLE 8

2,5-dibromophenyl-β,β',β''-trichloroethyl sulfone

A solution of 33 g 2,5-dibromobenzene sulfonyl chloride in 80 ml methylene chloride, 40 g vinylidene chloride, 0.2 g cupric chloride, 0.2 g copper bronze, 0.3 g triethyl amine hydrochloride and 20 ml acetonitrile were sealed in a glass lined autoclave. The autoclave was kept at 120° C. for 12 hours. After cooling, the reaction mixture was washed with 15% HCl solution, until it was colorless, than it was washed with water and dried over sodium sulphate. After removal of solvent by distillation, the product was recrystallized from isopropanol. Yield: 60%, M.P.: 114° C.

EXAMPLE 9

2,5-dichlorophenyl-β-chloro-β'-p-bromophenyl ethyl sulfone

In a similar manner to Example 5, 2,5-dichlorobenzene sulfonylchloride was reacted with p-bromostyrene to obtain the above product. M.P. 109° C.

EXAMPLE 10

2,5-dichlorophenyl-β-carboxymethyl vinyl sulfone

To a solution of 3.3 g of 2,5-dichlorophenyl-β-carboxymethyl-β-chloroethyl sulfone (Example 3) in 50 ml methylene chloride there was added 1 g triethylamine. After 10 minutes at room temperature the mixture was washed with water and then dried over sodium sulfate. On removal of the solvent, the product 2,5-dichlorophenyl-β-carboxymethyl vinyl sulfone was recovered and washed with ethanol. Yield: 75% M.P.: 82° C.

EXAMPLE 11

2,5-dibromophenyl-β,β'-dichlorovinyl sulfone

In a similar manner to Example 1, the 2,5-dibromophenyl-β,β'-dichlorovinyl sulfone was prepared starting with 2,5-dibromophenyl sulfonyl chloride and vinylidene chloride.

USES OF COMPOUNDS OF THE PRESENT INVENTION

The following description illustrates some of the possible uses of the novel compounds of the present invention.

The compounds of the present invention can be used as agricultural fungicides. They can be applied together with inert solids to form dusts, or can be suspended in a suitable liquid diluent, preferably water.

There can also be added surface active agents or wetting agents and/or inert solids in the liquid formulations. In such cases the active ingredient can be from 0.01 to 95% by weight of the entire composition. A preferred range in 0.1% to 25% by weight.

In place of water there can be employed organic solvents as carriers, e.g. hydrocarbons such as benzene, toluene, xylene, kerosene, diesel oil, fuel oil, and petroleum naphtha, ketones such as acetone, methyl ethyl ketone and cyclohexane, chlorinated hydrocarbons such as carbon tetrachloride, chloroform, trichloroethylene and perchloroethylene, esters such as ethyl acetate, amyl acetate and butyl acetate, glycol ether, e.g. monomethyl ether of ethylene glycol and monomethyl ether of diethylene glycol, alcohols, e.g. ethanol, isopropanol and amyl alcohols etc.

The sulfones can also be applied along with inert solid fungicidal adjuvants or carriers such as talc, pyrophyllite, synthetic fine silica Attaclay, kieselguhr, chalk, diatomaceous earth, calcium carbonate, bentonite, fuller's earth, cotton-seed hulls, wheat flour, soybean flour, etc. pumice, tripoli, wood flour, walnut shell flour, redwood flour, and lignin.

It is frequently desirable to incorporate a surface active agent in the pesticidal composition of this invention. Such surface active agents are advantageously employed in both the solid and liquid compositions. The surface active agent can be anionic, cationic or nonionic in character. The pH ought not to exceed about pH 11.

Typical classes of surface active agents include alkyl sulfonates, alkylaryl sulfonates, alkyl sulfates, alkylamide sulfonates, alkylaryl polyether alcohols, fatty acid esters of polyhydric alcohols, ethylene oxide addition products of such esters; addition production of long chain mercaptans and ethylene oxide; sodium alkyl benzene sulfonates having 14 to 18 carbon atoms, alkylphenolethylene oxides, for example, p-isoctyl phenol condensed with 10-ethylene oxide units; and soaps for example, sodium stearate and sodium oleate.

The solid and liquid formulations can be prepared by any suitable method. Thus, the active ingredients, in finely divided form of a solid, may be tumbled together with finely divided solid carrier. Alternatively, the active ingredient in liquid form, including solutions, dispersions, emulsions and suspensions thereof may be admixed with the solid carrier in finely divided form in amounts small enough to preserve the free-flowing property of the final dust composition.

Fungitoxicity towards soil fungi

Tests were carried out to demonstrate the fungitoxicity of some of the compounds in culture media.

Acetone solutions of the compound were mixed with an aliquot of distilled water and the fine suspension obtained was mixed with cooled but melted agar medium and poured into Petri dishes.

The tested fungi were grown on the solidified media. Growth of the fungus was measured and percent inhibition was calculated by comparing with the appropriate acetone-water controls. Media were usually Martin's or potato-dextrose agar media.

Typical results are shown in the following Table:

$ED_{50}$ of seven compounds tested on six soil fungi:

| Ex. | Rhizoctonia solani | Rhizoctonia batatiicola | Fusarium oxysporum sp. f.lycopersici | Sclerotinia rolfsil | Rhizopus stolonifer | Pythium aphanidermatum |
| --- | --- | --- | --- | --- | --- | --- |
| 1 | 5 | 5 | 50 | 10 | 50 | 10 |
| 2 | 10 | 10 | 50 | 10 | | 5 |
| 3 | 20 | 50 | >50 | 50 | >50 | >50 |
| 4 | 5 | 5 | 5 | 10 | | 1 |
| 5 | 20 | 50 | >50 | | | |
| 6 | 10 | 20 | >50 | | | |
| 7 | 5 | 20 | 50 | | 50 | |

$ED_{50}$ = effective dose, sufficient for the 50% inhibition of growth of the fungus, expressed in p.p.m.

Fungicidal activity of 2,5-dichlorophenylββ dichloro vinyl sulfone (example 4) in greenhouse tests:

Pythium

An aqueus suspension of the test compound was mixed with soil naturally infested with plant pathogen the fungus Pythium. As control water was used. Bean seeds were sown in the tested soil and the incidence of disease in the emerging seedlings was recorded during 21 days. Re-isolation from diseased seedlings confirmed the presence of Pythium.

Results: control of the disease was obtained at a concentration of 2 p.p.m.

Fusarium oxysporum f. sp. lycopersici

An aqueus suspension of the test compound with non-infested soil. Water was used as control. Tomato seedlings were pricked out from seedbeds, washed and then their roots were dipped in an inoculum suspension of a virulent isolate of the pathogen. The seedlings were then transplanted in the soil samples. The incidence of disease was recorded during 21 days. Re-isolation of the diseased seedlings confirmed the presence of Fusarium.

Control of disease was obtained at a concentration of 10 p.p.m.

Control of apple scab, *Venturia inaequalis* with six compounds in greenhouse test:

Apple seedlings were inoculated with the pathogen were rated for disease severity 15 days after inoculation. Leaves 4,5,6,7,8 from the terminal were rated according to Barrat & Horsfall Scale were

| | |
|---|---|
| 1–0% | leaf scabbed |
| 12–100% | leaf scabbed |

Mean disease severity at indicated treatment rates in p.p.m.:

| Example | 500 | 100 | 50 |
|---|---|---|---|
| 1 | 1.0 | 3.0 | 3.5 |
| 2 | 1.3 | 2.9 | 5.0 |
| 5 | 3.5 | 2.3 | 6.0 |
| 6 | 1.0 | 1.0 | 4.0 |
| 7 | 5.0 | 5.3 | 5.7 |
| 8 | 1.3 | 2.0 | 6.0 |
| Mancozeb | | 2.9 | 3.2 |

(a fungicide whose active ingredient is a coordination product of Maneb (ethylene bis (dithiocarbamato) Mn, containing 16 to 20% Mn and 2 to 2.5% Zn)

Comparative performance of 2 compounds and 2 commercial fungicides:

Spray treated plants were held in the greenhouse until the deposit dried and then inoculated with inoculum of known spore density.

Test 1  $2.5 \times 10^5$/ml
Test 2  $5.0 \times 10^5$/ml

| | Disease control expressed in % | | |
|---|---|---|---|
| Example | rate in p.p.m. | Test No.1 | Test No.2 |
| 1 | 50 | 63.6 | 98.2 |
| | 100 | 97.4 | 99.5 |
| | 500 | 100 | 100 |
| 8 | 50 | 86.4 | 99.9 |
| | 100 | 97.4 | 100 |
| | 500 | 100 | 99.9 |
| Cyprex (a fungicide based on n-dodecyl-guanidine acetate) | 50 | 89.4 | 0 |
| | 100 | 68 | 45 |
| | 500 | 81.8 | 71.4 |
| Benlate (a fungicide, the active ingredient of which is methyl 1-(butylcarbamoyl) benzimidazol-2-yl carbamate | 50 | 98.8 | 91.2 |
| | 100 | 100 | 100 |
| | 500 | | 100 |

Activity against common moulds on plasticized PVC sheets

The compounds of the present invention may also be incorporated into plastics such as PVC, particularly plasticized PVC, or into coatings and paints, or they may be applied to cloth or leather, to impart antifungal properties.

Complete inhibition of the growth of common moulds on PVC sheets plasticized with 30% dialkyl sebacate was affected on addition of 0.5% by weight of Example 3.

Antifungal tests on moulds of the type known to attack certain plasticized PVC, when Example 3 was incorporated.

The sheetings were 7 thou. millings of the following formulations

| | |
|---|---|
| PVC | 100 |
| DOS (dioctylsebacate) | 50 |
| Irgastab BC26 (for plasticized PVC) | 2 |

The antifungal agent was incorporated at 0.1, 0.5 and 1% on total formulation. In addition a control material without the antifungal agent was provided and also a reference sheeting containing 3% Estabex ABF, a commercial fungicide having plasticizing and stabilizing effects on plasticized PVC, and based on an epoxidized soya-bean oil and 10,10'-bisphenoxy-arsine. All % is by weight.

Halo test measured:

(1) Zones of growth inhibition in millimetres (halos);
(2) Estimation of growth under test sample (GUS).

Halo Test: Common moulds with pure cultures of:

*Penicillium funiculosum*
*Trichoderma viride*
*Aspergillus flavus*
*Aspergillus niger*
*Cladosporium cladosporoides*
*Paecilomyces varioti*
*Alternaria tenuis*

Blank sheeting without any agent showed no demonstrable fungistatic activity.

Sheeting containing 3% Estabex gave good level of activity.

Sheeting containing Example 3 at 0.5 and 1.0% produced a virtual complete inhibition of fungal attack.

| | Halo test: Common Moulds. | | | | | | | | | | | | | |
|---|---|---|---|---|---|---|---|---|---|---|---|---|---|---|
| | Zones of growth inhibition in millimetres (Halos) and estimation of growth under the test sample (GUS). | | | | | | | | | | | | | |
| | P. funiculosum | | T. viride | | A. flavus | | A. niger | | C. clados | | P. varioti | | A. tenuis | |
| Example | halo | GUS | halo | GUS | halo | GUS | halo | GUS | halo | GUS | halo | GUS | halo | GUS |
| 1 0.5% | (1) | + | 0 | + | 0 | ∓ | (1) | ∓ | 5 | − | 0 | + | 11 | − |
| 1% | 2.5 | ∓ | 0 | + | 0 | ∓ | 6 | − | 12 | − | 15 | − | 17 | − |
| 2 0.5% | 0 | + | 0 | + | 0 | + | 0 | + | (1) | ∓ | 0 | + | (7) | ∓ |
| 1% | 0 | + | 0 | + | 0 | + | 0 | + | 8 | − | 0 | + | (16) | − |
| 3 0.5% | 4 | − | 2 | ∓ | 1 | ∓ | 2 | − | 4 | − | 5 | − | 5 | − |
| 1% | 8 | − | 5 | ∓ | 1 | ∓ | 6 | − | 9 | − | 10 | − | 10 | − |
| Estabex 3% | 21 | − | 18 | − | 18 | − | 25 | − | 29 | − | 23 | − | 30 | − |

+ no reduction in growth;
± slight reduction in growth;
∓ moderate reduction in growth;
− complete reduction in growth.
Figures in brackets denote zones of inhibition of growth around the sample, where growth is partially but incompletely suppressed.
It is emphasized that in this test, halo size is dependent not only on antifungal activity but also on diffusability through agar.
Sheeting containing 0.5% Example 3 all fungi were inhibited and at 1.0% the degree of inhibition against the seven fungi was good.

Weight Loss Test: Duplicate sets of three weighed 6 cm × 1 cm strips of the PVC sheeting on mineral salts-agar growth medium were inoculated with a mixed spore suspension of: *Aspergillus flavus, Aspergillus niger, Paecilomyces varioti, Penicillium funiculosum, Trichoderma viride, Alternaria tenuis, Cladosporum cladosporoides.*

A single set of three strips treated with mercuric chloride to prevent microbial growth served as experimental control. Losses in weight were determined after 14 days incubation at 28° C.

| | | % weight loss | Mean % | Mean % loss as plasticizer |
|---|---|---|---|---|
| Example 3 | | 0.7 | | |
| | | 0.6 | | |
| | | 0.4 | | |
| | 0.5% | | 0.6 | 1.8 |
| | | 0.7 | | |
| | | 0.6 | | |
| | | 0.5 | | |
| Example 3 | | 0.4 | | |
| | | 0.1 | | |
| | | 0.01 | | |
| | 1.0% | | 0.2 | 0.6 |
| | | 0.2 | | |
| | | 0.1 | | |
| | | 0.1 | | |
| | | 0.1 | | |
| | | 0.1 | | |
| Estabex | | 0.1 | | |
| | 3% | | 0.1 | 0.3 |
| | | 0.1 | | |
| | | 0.1 | | |
| | | 0.1 | | |

Samples treated with mercuric chloride showed only negligible changes in weight.

Sheeting without agent showed significant amount of biodegradation, having lost some 38% of its plasticizer due to fungal attack.

Sheeting containing 3% Estabex showed no significant loss due to fungal attack.

Agar incorporation test

Pure cultures of fungi *Paecilomyces varioti, Cladosporium cladosporides, Penicillium funivulosum,* and *Aspergillus niger* were exposed to a range of dilutions of the compound viz: 10,000, 3,000, 1,000, 600, 300, 100, 30, 10, 1 ppm incorporated into agar via 2-methoxymethanol. The fungal plates were incubated for 5 days at 28° C. The plates were then assessed for either the presence or absence of growth and the minimum inhibitory concentration (MIC) in ppm recorded.

| | MIC in ppm. (mg/1) | | | |
|---|---|---|---|---|
| Compound | P. varioti | C. cladosporides | P. funiculosum | A. niger |
| Example 3 (2,5-dichlorophenyl β-carboxymethyl β-chloroethyl sulfone) | 100 | 100 | 30 | 100 |

We claim:

1. A 2,5-dihalophenyl-β-substituted sulfone of the formula $$\underset{X}{\overset{X}{\underset{\phantom{X}}{\text{C}_6\text{H}_3}}}-\text{SO}_2-Q$$

wherein Q is selected from $$-\text{CH}_2-\underset{\text{Cl}}{\overset{Y}{\text{C}}}-Z \text{ and } -\text{CH}=\text{C}\overset{Y}{\underset{Z}{\diagdown}},$$

wherein
X designates chlorine or bromine,
Y designates hydrogen, chlorine, or bromine,
Z designates chlorine, bromine, phenyl, halophenyl or —COOR where
R is lower alkyl of up to and including 4 carbom atoms,
Z' designates chlorine, bromine or —COOR, where R is lower alkyl of up to and including 4 carbon atoms,
provided that when Y designates hydrogen, Z' is —COOR as defined above.

2. Compounds according to claim 1, of the formula

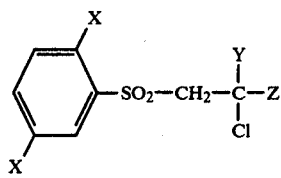

wherein X, Y and Z are as defined in claim 1.

3. Compounds according to claim 1, of the formula

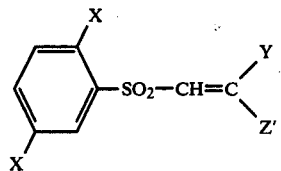

wherein X, Y, and Z' are as defined in claim 1.

4. A compound according to claim 2, wherein X is chlorine.

5. A compound according to claim 2, wherein X is bromine.

6. A compound according to claim 2, wherein X is chlorine, Y designates hydrogen and Z designates chlorine.

7. A compound according to claim 2, wherein X designates chlorine, Y and Z each designate chlorine.

8. A compound according to claim 2, wherein X designates chlorine, Y is hydrogen and Z is carboxymethyl.

9. A compound according to claim 3, wherein X is chlorine, and each of Y and Z' designates chlorine.

10. A compound according to claim 3, wherein X is chlorine, Y is hydrogen and Z' is carboxymethyl.

11. A fungicidal composition containing an inert carrier and, as the active ingredient thereof, a compound of the general formula

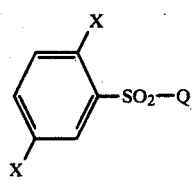

wherein Q is selected from

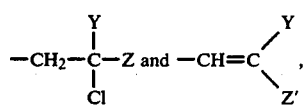

wherein
X designates chlorine or bromine,
Y designates hydrogen, chlorine or bromine,
Z designates chlorine, bromine, phenyl, halophenyl or —COOR where
R is lower alkyl of up to and including 4 carbom atoms,
Z' designates chlorine, bromine or —COOR, where R is lower alkyl of up to and including 4 carbon atoms, provided that when Y designates hydrogen, Z' is —COOR as defined above.

12. A fungicidal composition according to claim 11, wherein the compound is 2,5-dichlorophenyl-β,β'-dichloroethyl sulfone.

13. A fungicidal composition according to claim 11, wherein the compound is 2,5-dibromophenyl-β,β'-dichloroethyl sulfone.

14. A fungicidal composition wherein the compound is 2,5-dichlorophenyl-β,β'-dichlorovinyl sulfone.

15. A method for the control of fungi, which comprises applying to a substrate susceptible to attack by fungi a quantity of a compound defined in claim 1 sufficient to inhibit fungal attack of said substrate.

16. A polymeric composition resistant to fungal attack, comprising polyvinyl chloride incorporating as an additive a fungistatically active quantity of a compound defined in claim 1.

* * * * *

UNITED STATES PATENT OFFICE
CERTIFICATE OF CORRECTION

Patent No. 4,206,235　　　　　　　　　Dated June 3, 1980

Inventor(s) DAVID VOFSI et al.

It is certified that error appears in the above-identified patent and that said Letters Patent are hereby corrected as shown below:

Column 8, line.39: "(for plasticized PVC)" should read -- (a commercial stabilizer for plasticized PVC) --.

*Signed and Sealed this*

*Seventeenth* Day of *March 1981*

[SEAL]

*Attest:*

RENE D. TEGTMEYER

*Attesting Officer*　　　*Acting Commissioner of Patents and Trademarks*